(12) United States Patent
Woodley et al.

(10) Patent No.: US 11,883,329 B2
(45) Date of Patent: *Jan. 30, 2024

(54) CLOSED-LOOP LASER EYE SURGERY TREATMENT

(71) Applicant: AMO Development, LLC, Santa Ana, CA (US)

(72) Inventors: Bruce R. Woodley, Palo Alto, CA (US); Michael J. Simoneau, Morgan Hill, CA (US); Raymond Woo, Palo Alto, CA (US); Javier G. Gonzalez, Palo Alto, CA (US)

(73) Assignee: AMO Development, LLC, Irvine, CA (US)

( * ) Notice: Subject to any disclaimer, the term of this patent is extended or adjusted under 35 U.S.C. 154(b) by 253 days.

This patent is subject to a terminal disclaimer.

(21) Appl. No.: 17/307,964

(22) Filed: May 4, 2021

(65) Prior Publication Data
US 2021/0251807 A1  Aug. 19, 2021

Related U.S. Application Data

(60) Continuation of application No. 16/457,758, filed on Jun. 28, 2019, now Pat. No. 11,026,841, which is a
(Continued)

(51) Int. Cl.
*A61F 9/008* (2006.01)

(52) U.S. Cl.
CPC .......... *A61F 9/00829* (2013.01); *A61F 9/008* (2013.01); *A61F 9/00804* (2013.01);
(Continued)

(58) Field of Classification Search
CPC .. A61F 9/008; A61F 9/00802; A61F 9/00804; A61F 9/00806; A61F 9/00827;
(Continued)

(56) References Cited

U.S. PATENT DOCUMENTS

| 3,969,019 A | 7/1976 | Nohda |
| 5,674,233 A | 10/1997 | Dybbs |

(Continued)

FOREIGN PATENT DOCUMENTS

| JP | 362109565 A | 5/1987 |
| JP | 2010528770 A | 8/2010 |
| WO | 2004058113 A1 | 7/2004 |

OTHER PUBLICATIONS

International Search Report and Written Opinion for Application No. PCT/US2015/065639, datedd Mar. 29, 2016, 13 pages.
(Continued)

*Primary Examiner* — Ahmed M Farah
(74) *Attorney, Agent, or Firm* — Johnson & Johnson Surgical Vision, Inc.

(57) ABSTRACT

A laser eye surgery system includes a laser to generate a laser beam. A topography measurement system measures corneal topography. A processor is coupled to the laser and the topography measurement system, the processor embodying instructions to measure a first corneal topography of the eye, A first curvature of the cornea is determined. A target curvature of the cornea that treats the eye is determined. A first set of incisions and a set of partial incisions in the cornea smaller than the first set of incisions are determined. The set of partial incisions is incised on the cornea by the laser beam. A second corneal topography is measured. A second curvature of the cornea is determined. The second curvature is determined to differ from the target curvature and a second set of incisions are determined. The second set of incisions is incised on the cornea.

12 Claims, 4 Drawing Sheets

Related U.S. Application Data division of application No. 14/968,783, filed on Dec. 14, 2015, now Pat. No. 10,357,399.

(60) Provisional application No. 62/113,189, filed on Feb. 6, 2015.

(52) U.S. Cl.
CPC ...... *A61F 9/00806* (2013.01); *A61F 9/00827* (2013.01); *A61F 2009/00851* (2013.01); *A61F 2009/00859* (2013.01); *A61F 2009/00872* (2013.01); *A61F 2009/00882* (2013.01); *A61F 2009/00897* (2013.01)

(58) Field of Classification Search
CPC ........ A61F 9/00829; A61F 2009/00851; A61F 2009/00859; A61F 2009/00861; A61F 2009/00872; A61F 2009/00878; A61F 2009/0088; A61F 2009/00882
USPC .............................. 606/4, 5, 10–12; 128/898
See application file for complete search history.

(56) References Cited

U.S. PATENT DOCUMENTS

| | | |
|---|---|---|
| 5,720,894 A | 2/1998 | Neev et al. |
| 5,957,915 A | 9/1999 | Trost |
| 5,984,916 A | 11/1999 | Lai |
| 6,019,472 A | 2/2000 | Koester et al. |
| 6,454,761 B1 | 9/2002 | Freedman |
| 6,467,906 B1 | 10/2002 | Alpins |
| 6,641,577 B2 | 11/2003 | Bille |
| 7,458,683 B2 | 12/2008 | Chernyak |
| 7,655,002 B2 | 2/2010 | Myers et al. |
| 7,717,907 B2 | 5/2010 | Ruiz et al. |
| 8,262,646 B2 | 9/2012 | Frey et al. |
| 8,350,183 B2 | 1/2013 | Vogel et al. |
| 8,377,047 B2 | 2/2013 | Dai |
| 8,382,745 B2 | 2/2013 | Naranjo-Tackman et al. |
| 8,414,564 B2 | 4/2013 | Goldshleger et al. |
| 8,740,889 B2 | 6/2014 | Bissmann et al. |
| 9,510,747 B2 | 12/2016 | Fabrikant |
| 10,357,399 B2 * | 7/2019 | Woodley ............. A61F 9/00806 |
| 10,369,053 B2 | 8/2019 | Srinivasan et al. |
| 10,485,704 B2 | 11/2019 | Scott et al. |
| 11,337,857 B2 * | 5/2022 | Srinivasan .......... A61F 9/00829 |
| 2010/0114077 A1 | 5/2010 | Dai |
| 2011/0319873 A1 | 12/2011 | Raksi et al. |
| 2011/0319875 A1 | 12/2011 | Oesel et al. |
| 2012/0016351 A1 | 1/2012 | Stobrawa et al. |
| 2014/0135747 A1 | 5/2014 | Donitzky et al. |
| 2014/0371771 A1 | 12/2014 | Kurtz et al. |
| 2015/0018674 A1 * | 1/2015 | Scott ..................... A61B 3/107 |
| | | 600/407 |
| 2016/0074125 A1 | 3/2016 | Raymond et al. |
| 2016/0106588 A1 | 4/2016 | Srinivasan et al. |
| 2016/0150952 A1 | 6/2016 | Raymond et al. |
| 2016/0302971 A1 | 10/2016 | Morley et al. |

OTHER PUBLICATIONS

Ren Q., et al., "Laser Refractive Surgery; A Review and Current Status," Optical Engineering, 1995, vol. 34 (3), pp. 642-660.

* cited by examiner

CLOSED-LOOP LASER EYE SURGERY TREATMENT

CROSS REFERENCE TO RELATED APPLICATIONS

This application is a continuation application of U.S. patent application Ser. No. 16/457,758, filed Jun. 28, 2019, allowed, which is a divisional application of U.S. patent application Ser. No. 14/968,783, filed Dec. 14, 2015, granted as U.S. patent Ser. No. 10/357,399 on Jul. 23, 2019, which is a non-provisional application and claims the benefit under 35 U.S.C. § 119(e) of U.S. Provisional Application Ser. No. 62/113,189, filed Feb. 6, 2015. The above referenced applications are incorporated herein in their entireties by reference.

The subject matter of this disclosure is related to the following patent applications: U.S. application Ser. No. 14/069,042; U.S. application Ser. No. 14/509,850; U.S. application Ser. No. 14/256,307; U.S. application Ser. No. 14/255,430, the entire contents of each of which are incorporated herein by reference and suitable for combination according to the embodiments disclosed herein.

BACKGROUND

Many patients have visual errors associated with the refractive properties of the eye, such as nearsightedness, farsightedness, and astigmatism. Nearsightedness occurs when light focuses in front of the retina, while farsightedness occurs when light refracts to a focus behind the retina. Astigmatism may occur when the corneal curvature is unequal in two or more directions.

There are numerous prior surgical approaches for reshaping the cornea. Over the years, surgical laser systems have replaced manual surgical tools in ophthalmic procedures. For instance, in the well-known procedure known as LASIK (laser-assisted in situ keratomileusis), a laser eye surgery system providing a near-infrared femtosecond laser is used to cut a flap in the cornea, and another laser system providing ultraviolet radiation is used for ablating and reshaping the anterior surface of the cornea to correct nearsightedness or farsightedness. Other surgical approaches for reshaping the cornea include all laser LASIK, femto LASIK, corneaplasty, astigmatic keratotomy, corneal relaxing incision (hereinafter "CM"), Limbal Relaxing incision (hereinafter "LRI"), photorefractive keratectomy (hereinafter "PKK") and Small Incision Lens Extraction (hereinafter "SMILE").

Incisions such as Astigmatic Keratotomy, Corneal Relaxing Incision (CRI), and Limbal Relaxing Incision (LRI), are made at a depth in the cornea in a well-defined manner so as to enable the cornea to become more spherical. Arcuate incisions are conical incisions made in the cornea. Typically, to prevent an incision from penetrating entirely through the cornea, an arcuate incision is made that does not penetrate the posterior surface of the cornea. Some laser eye surgery systems are capable of making intrastromal arcuate incisions using a laser so that the incision is completely contained within the thickness of the cornea, and does not penetrate either the anterior or posterior surfaces of the cornea.

For a given astigmatic distortion, nomograms (tables) are often consulted to prescribe the depth of the arcuate incision and the angle appropriate to correct astigmatism. These tables predict the curvature correction of the cornea as a function of the incision depth and position.

The mechanical properties of the cornea, however, vary from person to person. While there are available nomograms that attempt to account for these differences by including parameters such as age, sex, and intraocular pressure to provide a better estimate in treatment planning, these tables are constructed on a trial-and-error basis from observational evidence from refractive surgeries. Although more popular nomograms, such as the Abbott LIU calculator, are available, many doctors often generate their own nomograms based on their own surgical experience. Hence, there is no consensus on a benchmark nomogram. Furthermore, current astigmatism treatment is performed as an open loop process in that the treatment is not adjusted in response to changes in the curvature of the cornea. Thus, current treatment planning methods for astigmatism are simple and provide sub-optimal results.

Therefore, there is a need for improved surgical laser apparatus and methods of treatment planning for treating astigmatism of the eye.

SUMMARY OF THE INVENTION

Hence, to obviate one or more problems due to limitations or disadvantages of the related art, this disclosure provides embodiments for improved treatment of materials, including eye tissue, such as incisions made by a laser beam during laser eye surgery. In many embodiments, the incisions are made through laser-induced photodisruption. Although specific reference is made to cutting tissue for surgery, including eye surgery, the embodiments described here can be used in many ways with many materials as well as to treat materials, including for example, cutting optically transparent materials.

In some embodiments, corneal topography is measured in real time to adjust the astigmatism treatment in response to the laser incisions. Corneal deformation is measured while making the corneal incisions with the laser beam, and parameters are adjusted while the cuts are performed.

Embodiments provide improved eye surgery systems, and related methods. In one aspect, a laser eye surgery system includes a laser to generate a laser beam. A topography measurement system measures conical topography. A processor is coupled to the laser and the topography measurement system, wherein the processor comprises a tangible non-volatile computer recordable medium embodying instructions to measure a first corneal topography of the eye using the topography measurement system. A first curvature of the cornea based on the first corneal topography, as well as a target curvature of the cornea that treats the eye may be determined. A first set of incisions in the cornea may be determined to achieve the target curvature in the cornea. A set of partial incisions in the cornea smaller than the first set of incisions may also be determined. The set of partial incisions is made in the cornea using the beam generated by the laser.

A second corneal topography is measured using the topography measurement system following the set of partial incisions. A second curvature of the cornea is determined on the basis of the second corneal topography. The second curvature is determined to differ from the target curvature. A second set of incisions in the cornea is determined and is different from the first set of incisions to achieve the target curvature in the cornea. The second set of incisions on the cornea is performed using the beam generated by the laser.

After performing the second set of incisions, the processor of the system may further embody instructions to measure a third cortical topography using the topography measurement system. Based on the third corneal topography, a third curvature of the cornea is determined. This third curvature is determined to differ from the target curvature. A third set of incisions to achieve the target curvature in the cornea is determined. The third set of incisions is performed on the cornea using the laser beam generated by the laser.

After performing the third set of incisions, a fourth corneal topography is measured using the topography measurement system. Based on the fourth corneal topography, a fourth curvature of the cornea is determined. The fourth curvature is determined to achieve the target curvature.

In many embodiments, the first set of incisions and the second set of incisions are based on a nomogram. The set of partial incisions may be determined based on a predetermined uncertainty level of the nomogram. The second set of incisions may overlap the first set of incisions so as to deepen the first set of incisions. Alternatively, the second set of incisions may be parallel to the first set of incisions.

The corneal topography measurement may use optical coherence tomography imaging. The second corneal topography may optionally measure a volume of bubbles formed as a result of the set of partial incisions performed using the laser beam. The laser may be a femtosecond laser. The laser system may treat higher order aberrations of the eye.

In another embodiment, a method of treating an eye includes the steps of measuring a first corneal topography of the eye, determining a first curvature of the cornea based on the first corneal topography, and a target curvature of the cornea that treats the eye. A first set of incisions in the cornea are determined to achieve the target curvature in the cornea and a set of partial incisions in the cornea smaller than the first set of incisions. The set of partial incisions are performed on the cornea by a laser.

After performing the set of partial incisions, a second corneal topography is measured. Based on the second corneal topography, a second curvature of the cornea is determined. The second curvature is determined to differ from the target curvature. To achieve the target curvature, a second set of incisions in the cornea are determined that are different from the first set of incisions. The laser is used to perform the second set of incisions on the cornea.

After performing the second set of incisions, the method may further include the steps of measuring a third corneal topography. Based on the third corneal topography, a third curvature of the cornea may be determined. The third curvature may be determined to differ from the target curvature. To achieve the target curvature in the cornea, a third set of incisions are determined t. A laser is used to perform the third set of incisions on the cornea.

After performing the third set of incisions, a fourth corneal topography is measured. Based on the fourth corneal topography, a fourth curvature of the cornea is determined. The fourth curvature is determined to achieve the target curvature.

Optionally, the first set of incisions and the second set of incisions are based on a nomogram. The set of partial incisions may be determined based on a predetermined uncertainty level of the nomogram. The second set of incisions may overlap the first set of incisions so as to deepen the first set of incisions. Alternatively, the second set of incisions may be parallel to the first set of incisions.

The conical topography measurement may use optical coherence tomography imaging. The second corneal topography may also measure a volume of bubbles formed as a result of the set of partial incisions formed by the laser. In some embodiments, the laser may be a femtosecond laser, and the method may treat higher order aberrations of the eye.

This summary and the following detailed description are merely exemplary, illustrative, and explanatory, and are not intended to limit, but to provide further explanation of the invention as claimed. Additional features and advantages of the invention will be set forth in the descriptions that follow, and in part will be apparent from the description, or may be learned by practice of the invention. The objectives and other advantages of the invention will be realized and attained by structure particularly pointed out in the written description, claims and the appended drawings.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
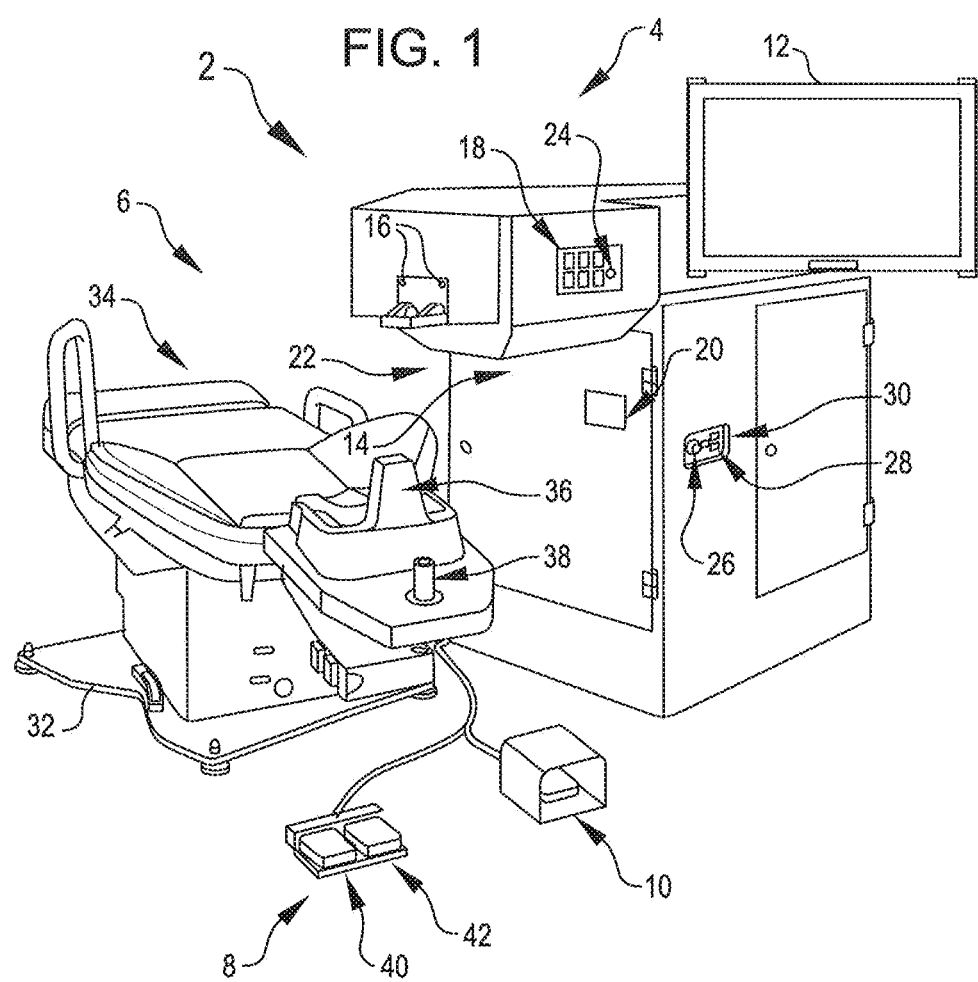
FIG. 1 is a perspective view showing a laser eye surgery system, in accordance with many embodiments.

The following description describes various embodiments of the present invention. For purposes of explanation, specific configurations and details are set forth so as to provide a thorough understanding of the embodiments. It will also, however, be apparent to one skilled in the art that embodiments of the present invention can be practiced without certain specific details. Further, to avoid obscuring the embodiment being described, various well-known features may be omitted or simplified in the description.

Methods and systems related to laser eye surgery, including in particular, laser eye surgery treatment planning and control, are disclosed. In many embodiments, a laser is used to form precise incisions to correct higher order aberrations, such as astigmatism. Although specific reference is made to tissue treatment for laser eye surgery, embodiments described herein can be combined in one or more of many ways with many surgical procedures and devices, such as orthopedic surgery, robotic surgery, as well as microkeratomes.

The embodiments described herein are particularly well suited for treating tissue, such as the surgical treatment of tissue. In many embodiments, the tissue comprises an optically transmissive tissue, such as eye tissue. The embodiments described here can be combined in many ways with one or more of many known surgical procedures such as cataract surgery, laser assisted in situ keratomileusis (hereinafter "LASIK"), laser assisted subepithelial keratectomy (hereinafter "LASE"). The embodiments described here are also particularly well-suited for retinal surgery.

The embodiments described here are particularly well-suited for treating astigmatism in the eye. In many embodiments, the laser eye surgery system comprises a processor having tangible medium embodying instructions for determining the strength and location of arcuate incisions that are generated by laser beam pulses in response to measured characteristics of the cornea. Methods and systems related to laser eye surgery are disclosed.

As used here, the terms anterior and posterior refers to known orientations with respect to the patient. Depending on the orientation of the patient for surgery, the terms anterior and posterior may be similar to the terms upper and lower, respectively, such as when the patient is placed in a supine position on a bed. The terms distal and anterior may refer to an orientation of a structure from the perspective of the user, such that the terms proximal and distal may be similar to the terms anterior and posterior when referring to a structure placed on the eye, for example. A person of ordinary skill in the art will recognize many variations of the orientation of the methods and apparatus as described herein, and the terms anterior, posterior, proximal, distal, upper, and lower are used merely by way of example.

This disclosure provides methods and apparatus for providing adjustment to compensate for variations in patient anatomy. The methods and systems disclosed may comprise closed loop control combined with a software look up table (hereinafter "LUT") embodied in a tangible medium. The LUT may include one or more nomograms, as well as the underlying data set used to generate the nomogram.

As used here, light encompasses electromagnetic radiation having one or more wavelengths in one or more of the ultraviolet, visible or infrared portions of the electromagnetic spectrum.

As used here, in situ encompasses position and refers to measurements and treatments made with an object located in substantially the same position.

FIG. 1 shows a laser eye surgery system 2, in accordance with many embodiments, operable to form precise incisions in the cornea, in the lens capsule, and/or in the crystalline lens nucleus. The system 2 includes a main unit 4, a patient chair 6, a dual function footswitch 8, and a laser footswitch 10.

The main unit 4 includes many primary subsystems of the system 2. For example, externally visible subsystems include a touch-screen control panel 12, a patient interface assembly 14, patient interface vacuum connections 16, a docking control keypad 18, a patient interface radio frequency identification (RIM) reader 20, external connections 22 (e.g., network, video output, footswitch, USB port, door interlock, and AC power), laser emission indicator 24, emergency laser stop button 26, key switch 28, and USB data ports 30.

The patient chair 6 includes a base 32, a patient support bed 34, a headrest 36, a positioning mechanism, and a patient chair joystick control 38 disposed on the headrest 36. The positioning control mechanism is coupled between the base 32 and the patient support bed 34 and headrest 36. The patient chair 6 is configured to be adjusted and oriented in three axes (x, y, and z) using the patient chair joystick control 38. The headrest 36 and a restrain system (not shown, e.g., a restraint strap engaging the patient's forehead) stabilize the patient's head during the procedure. The headrest 36 includes an adjustable neck support to provide patient comfort and to reduce patient head movement. The headrest 36 is configured to be vertically adjustable to enable adjustment of the patient head position to provide patient comfort and to accommodate variation in patient head size.

The patient chair 6 allows for tilt articulation of the patient's legs, torso, and head using manual adjustments. The patient chair 6 accommodates a patient load position, a suction ring capture position, and a patient treat position. In the patient load position, the chair 6 is rotated out from under the main unit 4 with the patient chair back in an upright position and patient footrest in a lowered position. In the suction ring capture position, the chair is rotated out from under the main unit 4 with the patient chair back in reclined position and patient footrest in raised position. In the patient treat position, the chair is rotated under the main unit 4 with the patient chair back in reclined position and patient footrest in raised position.

The patient chair 6 is equipped with a "chair enable" feature to protect against unintended chair motion. The patient chair joystick 38 can be enabled in either of two ways. First, the patient chair joystick 38 incorporates a "chair enable" button located on the top of the joystick. Control of the position of the patient chair 6 via the joystick 38 can be enabled by continuously pressing the "chair enable" button. Alternately, the left foot switch 40 of the dual function footswitch 8 can be continuously depressed to enable positional control of the patient chair 6 via the joystick 38.

In many embodiments, the patient control joystick 38 is a proportional controller. For example, moving the joystick a small amount can be used to cause the chair to move slowly. Moving the joystick a large amount can be used to cause the chair to move faster, Holding the joystick at its maximum travel limit can be used to cause the chair to move at the maximum chair speed. The available chair speed can be reduced as the patient approaches the patient interface assembly 14.

The emergency stop button 26 can be pushed to stop emission of all laser output, release vacuum that couples the patient to the system 2, and disable the patient chair 6. The stop button 26 is located on the system front panel, next to the key switch 28.

The key switch 28 can be used to enable the system 2. When in a standby position, the key can be removed and the system is disabled. When in a ready position, the key enables power to the system 2.

The dual function footswitch 8 is a dual footswitch assembly that includes the left foot switch 40 and a right foot switch 42. The left foot switch 40 is the "chair enable" footswitch. The right footswitch 42 is a "vacuum ON" footswitch that enables vacuum to secure a liquid optics interface suction ring to the patient's eye. The laser footswitch 10 is a shrouded footswitch that activates the treatment laser when depressed while the system is enabled.

In many embodiments, the system 2 includes external communication connections. For example, the system 2 can include a network connection (e.g., an RJ45 network connection) for connecting the system 2 to a network. The network connection can be used to enable network printing of treatment reports, remote access to view system performance logs, and remote access to perform system diagnostics. The system 2 can include a video output port (e.g., HDMI) that can be used to output video of treatments performed by the system 2. The output video can be displayed on an external monitor for, for example, viewing by family members and/or training. The output video can also be recorded for, for example, archival purposes. The system 2 can include one or more data output ports (e.g., USB) to, for example, enable export of treatment reports to a data storage device. The treatments reports stored on the data storage device can then be accessed at a later time for any suitable purpose such as, for example, printing from an external computer in the case where the user without access to network based printing.

Figure 2:
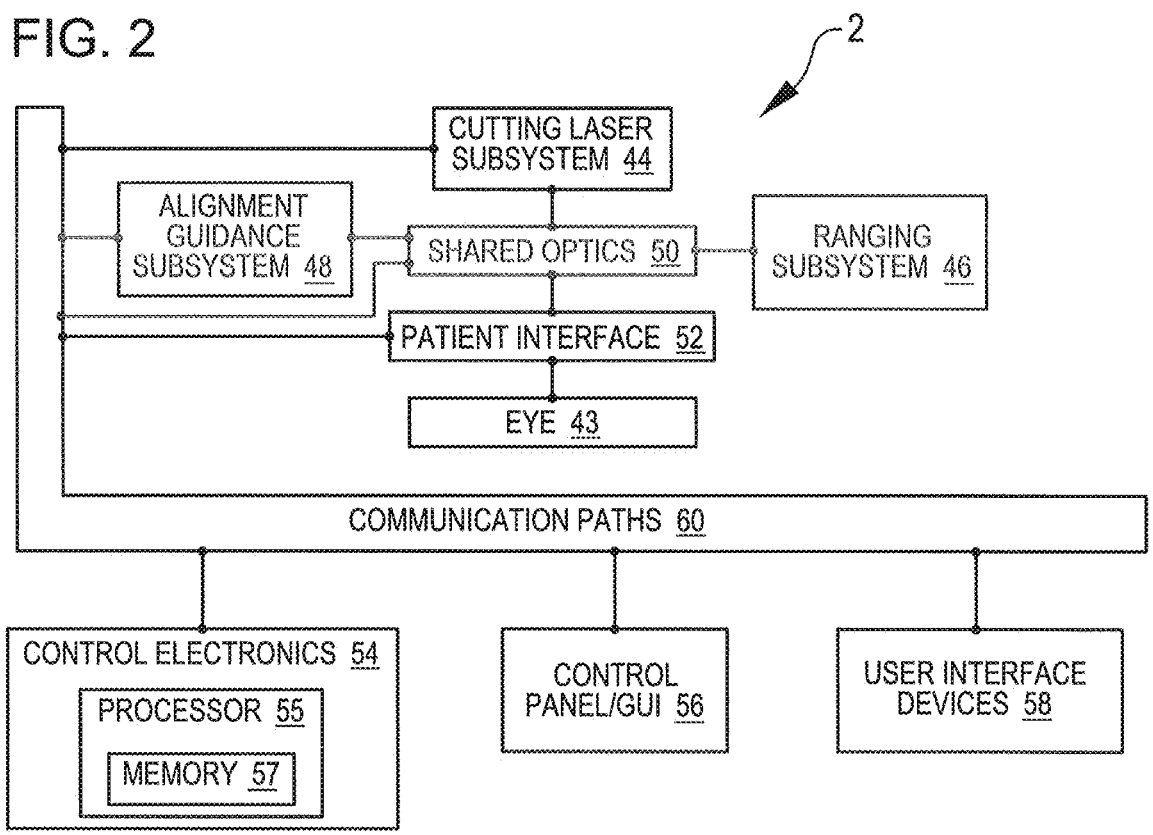
FIG. 2 is a simplified block diagram showing a top level view of the configuration of a laser eye surgery system, in accordance with many embodiments.

FIG. 2 shows a simplified block diagram of the system 2 coupled with a patient eye 43. The patient eye 43 comprises a cornea, a lens, and an iris. The iris defines a pupil of the eye 43 that may be used for alignment of eye 43 with system 2. The system 2 includes a cutting laser subsystem 44, a ranging subsystem 46, an alignment guidance system 48, shared optics 50, a patient interface 52, control electronics 54, a control panel/GUI 56, user interface devices 58, and communication paths 60. The control electronics 54 is operatively coupled via the communication paths 60 with the cutting laser subsystem 44, the ranging subsystem 46, the alignment guidance subsystem 48, the shared optics 50, the patient interface 52, the control panel/GUI 56, and the user interface devices 58.

In many embodiments, the cutting laser subsystem 44 incorporates femtosecond (FS) laser technology. By using femtosecond laser technology, a short duration e.g., approximately $10^{-13}$ seconds in duration) laser pulse (with energy level in the micro joule range) can be delivered to a tightly focused point to disrupt tissue, thereby substantially lowering the energy level required as compared to the level required for ultrasound fragmentation of the lens nucleus and as compared to laser pulses having longer durations.

The cutting laser subsystem 44 can produce laser pulses having a wavelength suitable to the configuration of the system 2. As a non-limiting example, the system 2 can be configured to use a cutting laser subsystem 44 that produces laser pulses having a wavelength from 1020 nm to 1050 nm. For example, the cutting laser subsystem 44 can have a diode-pumped solid-state configuration with a 1030 (+/−5) nm center wavelength.

The cutting laser subsystem 44 can include control and conditioning components. For example, such control components can include components such as a beam attenuator to control the energy of the laser pulse and the average power of the pulse train, a fixed aperture to control the cross-sectional spatial extent of the beam containing the laser pulses, one or more power monitors to monitor the flux and repetition rate of the beam train and therefore the energy of the laser pulses, and a shutter to allow/block transmission of the laser pulses. Such conditioning components can include an adjustable zoom assembly to adapt the beam containing the laser pulses to the characteristics of the system 2 and a fixed optical relay to transfer the laser pulses over a distance while accommodating laser pulse beam positional and/or directional variability, thereby providing increased tolerance for component variation.

The ranging subsystem 46 is configured to measure the spatial disposition of eye structures in three dimensions. The measured eye structures can include the anterior and posterior surfaces of the cornea, the anterior and posterior portions of the lens capsule, the iris, and the limbus. In many embodiments, the ranging subsystem 46 utilizes optical coherence tomography (OCT) imaging. As a non-limiting example, the system 2 can be configured to use an OCT imaging system employing wavelengths from 780 nm to 970 nm. For example, the ranging subsystem 46 can include an OCT imaging system that employs a broad spectrum of wavelengths from 810 nm to 850 nm. Such an OCT imaging system can employ a reference path length that is adjustable to adjust the effective depth in the eye of the OCT measurement, thereby allowing the measurement of system components including features of the patient interface that lie anterior to the cornea of the eye and structures of the eye that range in depth from the anterior surface of the cornea to the posterior portion of the lens capsule and beyond.

The alignment guidance subsystem 48 can include a laser diode or gas laser that produces a laser beam used to align optical components of the system 2. The alignment guidance subsystem 48 can include LEDs or lasers that produce a fixation light to assist in aligning and stabilizing the patient's eye during docking and treatment. The alignment guidance subsystem 48 can include a laser or LED light source and a detector to monitor the alignment and stability of the actuators used to position the beam in X, Y, and Z. The alignment guidance subsystem 48 can include a video system that can be used to provide imaging of the patient's eye to facilitate docking of the patient's eye 43 to the patient interface 52. The imaging system provided by the video system can also be used to direct via the GUI the location of cuts. The imaging provided by the video system can additionally be used during the laser eye surgery procedure to monitor the progress of the procedure, to track movements of the patient's eye 43 during the procedure, and to measure the location and size of structures of the eye such as the pupil and/or limbus.

The shared optics 50 provides a common propagation path that is disposed between the patient interface 52 and each of the cutting laser subsystem 44, the ranging subsystem 46, and the alignment guidance subsystem 48. In many embodiments, the shared optics 50 includes beam combiners to receive the emission from the respective subsystem (e.g., the cutting laser subsystem 44, and the alignment guidance subsystem 48) and redirect the emission along the common propagation path to the patient interface. In many embodiments, the shared optics 50 includes an objective lens assembly that focuses each laser pulse into a focal point. In many embodiments, the shared optics 50 includes scanning mechanisms operable to scan the respective emission in three dimensions. For example, the shared optics can include an XY-scan mechanism(s) and a Z-scan mechanism. The XY-scan mechanism(s) can be used to scan the respective emission in two dimensions transverse to the propagation direction of the respective emission. The Z-scan mechanism can be used to vary the depth of the focal point within the eye 43. In many embodiments, the scanning mechanisms are disposed between the laser diode and the objective lens such that the scanning mechanisms are used to scan the alignment laser beam produced by the laser diode. In contrast, in many embodiments, the video system is disposed between the scanning mechanisms and the objective lens such that the scanning mechanisms do not affect the image obtained by the video system.

The patient interface 52 is used to restrain the position of the patient's eye 43 relative to the system 2. In many embodiments, the patient interface 52 employs a suction ring that is vacuum attached to the patient's eye 43, The suction ring is then coupled with the patient interface 52, for example, using vacuum to secure the suction ring to the patient interface 52. In many embodiments, the patient interface 52 includes an optically transmissive structure having a posterior surface that is displaced vertically from the anterior surface of the patient's cornea and a region of a suitable liquid (e.g., a sterile buffered saline solution (BSS) such as Alcon BSS (Alcon Part Number 351-55005-1) or an equivalent) is disposed between and in contact with the posterior surface and the patient's cornea and forms part of a transmission path between the shared optics 50 and the patient's eye 43. The optically transmissive structure may comprise a lens 96 having one or more curved surfaces. Alternatively, the patient interface 22 may comprise an optically transmissive structure having one or more substantially flat surfaces such as a parallel plate or wedge. In many embodiments, the patient interface lens is disposable and can be replaced at any suitable interval, such as before each eye treatment.

The control electronics 54 controls the operation of and can receive input from the cutting laser subsystem 44, the ranging subsystem 46, the alignment guidance subsystem 48, the patient interface 52, the control panel/GUI 56, and the user interface devices 58 via the communication paths 60. The communication paths 60 can be implemented in any suitable configuration, including any suitable shared or dedicated communication paths between the control electronics 54 and the respective system components.

The control electronics 54 can include any suitable components, such as one or more processor, one or more field-programmable gate array (FPGA), and one or more memory storage devices. In many embodiments, the control electronics 54 controls the control panel/GUI 56 to provide for pre-procedure planning according to user specified treatment parameters as well as to incorporate closed-loop control over the laser eye surgery procedure.

The control electronics 54 may comprise a processor/controller 55 (referred to herein as a processor) that is used to perform calculations related to treatment planning, system operation and provide control signals to the various system elements. A computer readable medium 57 (also referred to as a database or a memory) is coupled to the processor 55 in order to store data used by the processor and other system elements. The processor 55 interacts with the other components of the system as described more fully throughout the present specification. In an embodiment, the memory 57 can include a look up table that can be utilized to control one or more components of the laser system as described herein.

The processor 55 can be a general purpose microprocessor configured to execute instructions and data, such as a Pentium processor manufactured by the Intel Corporation of Santa Clara, Calif. It can also be an Application Specific Integrated Circuit (ASIC) that embodies at least part of the instructions for performing the method in accordance with the embodiments of the present disclosure in software, firmware and/or hardware. As an example, such processors include dedicated circuitry, ASICs, combinatorial logic, other programmable processors, combinations thereof and the like.

The memory 57 can be local or distributed as appropriate to the particular application. Memory 57 may include a number of memories including a main random access memory (RAM) for storage of instructions and data during program execution and a read only memory (ROM) in which fixed instructions are stored. Thus, memory 57 provides persistent (non-volatile) storage for program and data files, and may include a hard disk drive, flash memory, a floppy disk drive along with associated removable media, a Compact Disk Read Only Memory (CD-ROM) drive, an optical drive, removable media cartridges, and other like storage media.

The user interface devices 58 can include any suitable user input device suitable to provide user input to the control electronics 54. For example, the user interface devices 58 can include devices such as, for example, the dual function footswitch 8, the laser footswitch 10, the docking control keypad 18, the patient interface radio frequency identification (RFID) reader 20, the emergency laser stop button 26, the key switch 28, and the patient chair joystick control 38.

The system 2 can be set to locate the anterior and posterior surfaces of the lens capsule and cornea and ensure that the UF laser pulse beam 66 will be focused on the lens capsule and cornea at all points of the desired opening. Imaging modalities and techniques described herein, such as for example, Optical Coherence Tomography (OCT), and such as Purkinje imaging, Scheimpflug imaging, confocal or nonlinear optical microscopy, fluorescence imaging, ultrasound, structured light, stereo imaging, or other known ophthalmic or medical imaging modalities and/or combinations thereof may be used to determine the shape, geometry, perimeter, boundaries, and/or 3-dimensional location of the lens and lens capsule and cornea to provide greater precision to the laser focusing methods, including 2D and 3D patterning. Laser focusing may also be accomplished using one or more methods including direct observation of an aiming beam, or other known ophthalmic or medical imaging modalities and combinations thereof, such as but not limited to those defined above.

Optical imaging of the cornea, anterior chamber, and lens can be performed using the same laser and/or the same scanner used to produce the patterns for cutting. Optical imaging can be used to provide information about the axial location and shape (and even thickness) of the anterior and posterior lens capsule, the boundaries of the cataract nucleus, as well as the depth of the anterior chamber and features of the cornea. This information may then be loaded into the laser 3-D scanning system or used to generate a three dimensional model/representation/image of the cornea, anterior chamber, and lens of the eye, and used to define the cutting patterns used in the surgical procedure.

Figure 3:
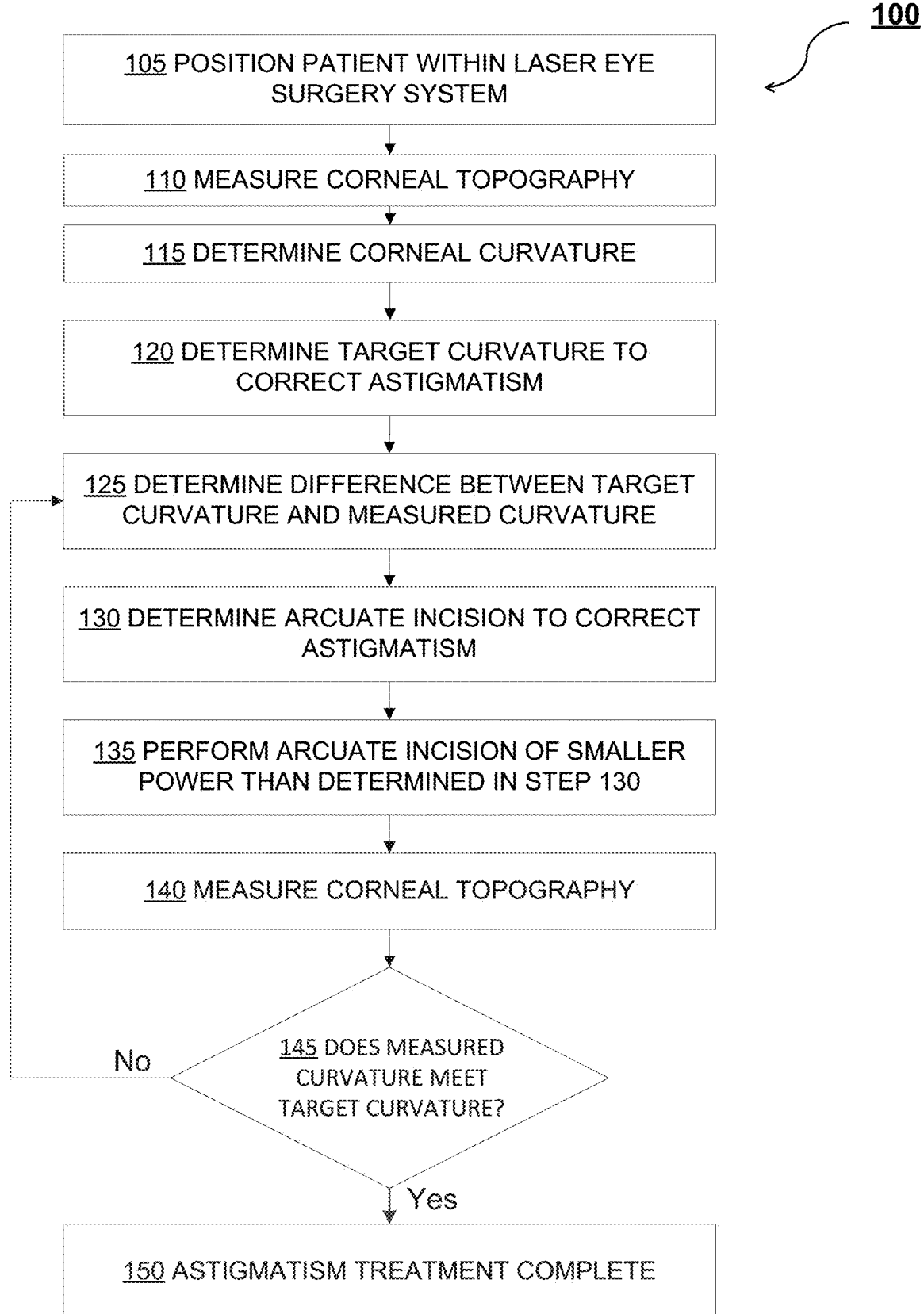
FIG. 3 shows a flow chart of a method for treating the eye, in accordance with many embodiments.
Figure 4A:
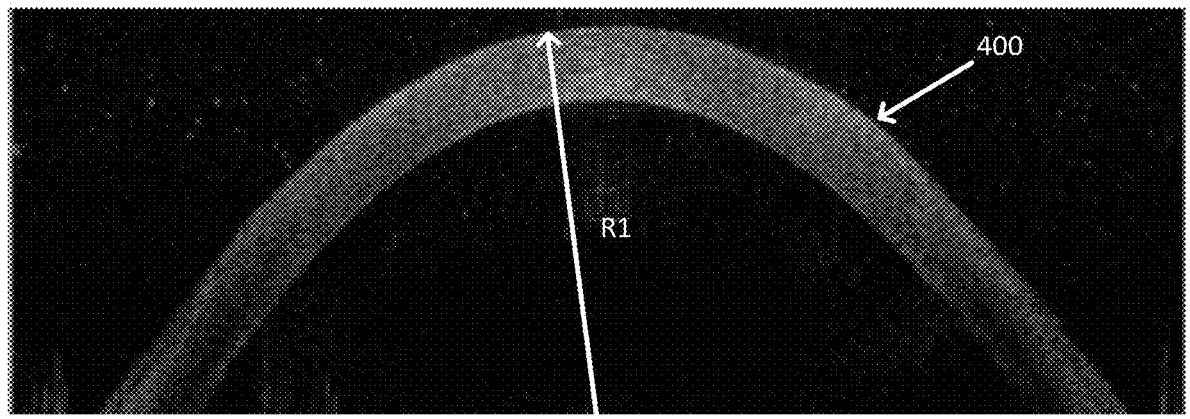
FIGS. 4A-4B are GUI displays illustrating the method of FIG. 3, in accordance with many embodiments.
Figure 4B:
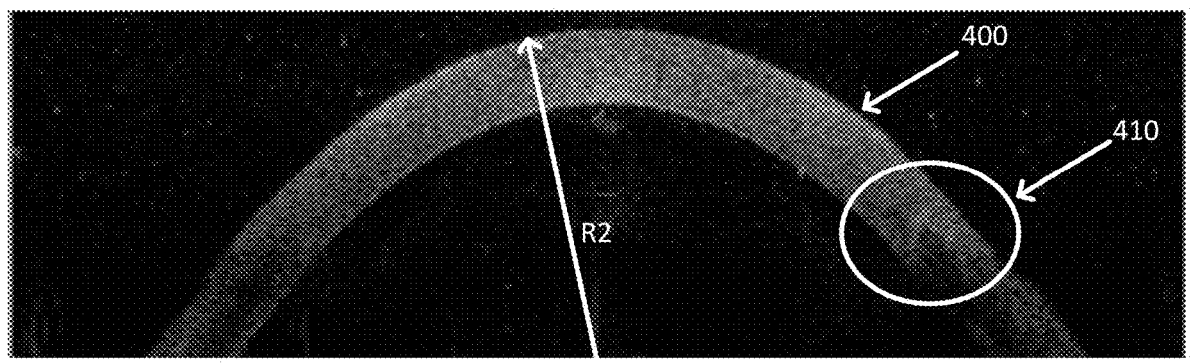

FIG. 3 shows a flow chart of a method 100 for treating an eye, in accordance with embodiments, FIGS. 4A-4B are GUI displays illustrating the method of FIG. 3, in accordance with many embodiments. In a non-limiting exemplary embodiment discussed below, the eye treatment is a laser eye surgery for astigmatism treatment, although the eye treatment may comprise any higher order aberration. The method 100 provides closed loop control of astigmatism treatment by adjusting the arcuate incision parameters as a function of the deformation of the cornea during cutting. The method 100 comprises the following main steps:

In a step 105, the patient is positioned within an operable range laser eye surgery system 2 described herein. Specifically, the patient's cornea is positioned within a capture range of the measurement system of the laser eye surgery system 2. Positioning of the patient for laser surgery is typically enabled by motion of the patient bed 34 or by motion of the laser system 2 where the eye, and specifically the cornea, is placed within the operative range of the measurement system. This can be accomplished with the use of subsystems of the laser system 2 described herein such as alignment guidance system 48 of laser system 2.

In a step 110, the measurement system is used to measure a shape of the cornea by performing a first corneal topography. Such a measurement system may comprise the ranging subsystem 46 described above. The OCT system can be used to capture an iris image of the eye and measure the axial position of the cornea. Corneal power can be measured from camera images of reflected light from the cornea.

In the measurement step 110, multiple OCT or other scans of the cornea surfaces can be acquired sequentially in a short time. Multiple scans can increase the confidence of obtaining good data. Post-processing of the scans can remove potential eye motion and further improve the measurement accuracy. The ranging subsystem 46 may apply other modalities for mapping the ocular surfaces such as a keratometry system, Placido imaging, Hartmann-shack wavefront sensing, confocal tomography, low coherence reflectometry, among others.

In the step 115, a first curvature of the cornea along the two principle axes, the steep axis direction, and the magnitude in dieters of the patient's astigmatism are determined based on the measured first corneal topography. Fitting algorithms can be used to calculate commonly used parameters of the cornea. Examples of fitting algorithms suitable for mapping optical tissue surfaces include elliptical surfaces, Fourier transforms, polynomials, spherical harmonics, Taylor polynomials, a wavelet transform, or Zernike polynomials. Commonly used parameters include the optical power of the cornea, astigmatic axis angle, and astigmatism magnitude. The laser system 2 comprises a subsystem, such as the ranging subsystem 46, for mapping the ocular surfaces that are being treated having an OCT system described herein which may be used to visualize and image the eye. FIG. 4A is a GUI display illustrating a cross-sectional view of the cornea 400 having a measured radius of curvature $R_1$.

In some embodiments, other features of the eye may be determined. For instance, a thickness profile of the eye and treatment axes of the eye are determined. The natural pupil and pupil center of the eye may be identified. Also, one or more tissue structures of the eye may be identified that comprise one or more of a limbus, sclera, blood vessels, iris, pupil, pupil center, natural pupil, natural pupil center, cornea, cornea anterior surface, astigmatic axes of cornea anterior surface, cornea posterior surface, thickness profile of cornea, vertex of cornea, lens, lens anterior surface, astigmatic axes of lens anterior surface, lens posterior surface, astigmatic axis of lens posterior surface, retina, anterior optical node of eye, posterior optical node of eye, optical axis of eye, line of sight of eye, pupillary axis of eye, visual axis of eye, nodal axis of eye, center of curvature of anterior corneal surface, center of curvature of posterior corneal surface, center of curvature of lens anterior surface, or lens posterior surface.

In a step 120, a target curvature of the cornea to correct the measured astigmatism is determined. This may be performed by consulting a nomogram or other look-up table stored within the memory 57 of system 2. The nomogram can be based on the curvature of the surface rather than the position of the surface itself.

Then, a differential assessment is performed at step 125 between the measured cornea curvature and the target ideal cornea curvature. In step 130, parameters of a first set of arcuate incisions to be performed are determined based on a nomogram and the direction and magnitude of the patient astigmatism. The determined first set of arcuate incisions are intended to modify the cornea to achieve the target cornea curvature and includes a depth, length and location and a number of incisions. Optionally, the system 2 may receive user input from a user interface device 58 of the first arcuate incision parameters.

In a step 135, a partial incision smaller than that of the first incision of step 130 is determined. The partial incision is not intended to modify the cornea curvature to achieve the target curvature and may be determined on a predetermined percentage basis. For example, the partial incision may be half or three-quarters the size of the first incision determined in step 130.

In some embodiments, the partial incision may be determined based on a predetermined uncertainty level. Uncertainty is a quantification of the doubt about the measurement result, which in this case is the nomogram value. Nomograms may vary in quality due to a number of factors, including the size of the data set from which the nomogram is generated from. For instance, given a set of input parameters such as age, sex, and intraocular pressure, etc., a nomogram provides a set of incision parameters as a best fit to the underlying data set. However, the underlying data set may provide a range of incision parameters that may be expressed in terms of uncertainty boundaries. The level of uncertainty may vary based on the quality of the data.

Once the uncertainty boundaries are determined from a nomogram data set, the partial incisions may be set to correspond to the incision parameters at a predetermined uncertainty level that undershoots the determined first set of arcuate incisions. For example, incision parameters at a 25% uncertainty level correspond to 25% of patients reaching the target astigmatism correction with the remaining 75% of patients not reaching the targeted astigmatism correction. Consequently, selection of a lower uncertainty level decreases the likelihood of astigmatism overcorrection and increases the likelihood that stepwise, incremental astigmatism correction is performed. The partial incision parameters may be based on a predetermined uncertainty level of the nomogram data. In other embodiments, a partial incision that is less than a first incision may be determined based on a standard deviation of the nomogram data.

The set of partial arcuate incisions are then performed on the cornea by the cutting laser subsystem 44 in step 135. FIG. 4B is a GUI display illustrating a cross-sectional view of the cornea 400 having a measured radius of curvature $R_1$ after a first set of partial incisions 410 are made to the cornea 400. By performing a set of partial arcuate incisions that will likely not completely correct astigmatism to a target value, subsequent corneal measurements are performed to provide feedback to adjust the incision during cutting to more accurately achieve a desired cornea curvature and astigmatism correction.

After the partial incision is performed in step 135, a second cortical topography measurement is performed in step 140 in a manner similar to that performed in step 110. A second curvature of the cornea is determined on the basis of the second corneal topography.

In the step 145, it is determined whether the second curvature differs from the target curvature. If the measured and target curvatures agree within a predetermined threshold, then the astigmatism is corrected to the desired level and the eye treatment is completed in step 150, The patient may be removed from the laser eye surgery system 2 or undergo another eye treatment procedure.

However, if the second curvature does not meet the target curvature in step 145, then the method returns to execute steps 125-140 until step 145 is satisfied. In this manner, the length and/or depth of the incision can be controlled in response to the measured change in topography.

If step 145 is not satisfied, a second differential assessment is performed at step 125 between the second measured cornea curvature of step 140 and the target cornea curvature of step 120. In step 130, a second set of arcuate incisions to achieve the target curvature in the cornea are determined by consulting the nomogram based on the second curvature of the cornea as formed after the first set of partial incisions are cut. The parameters of the second set of incisions are different from the parameters of the first set of incisions since the cornea has been modified by the first set of partial incisions.

In the step 135, a second set of partial incisions smaller than the second set of incisions of step 130 may be determined in the same manner as discussed above. The second set of partial incisions may be equal to, or smaller than the second set of incisions. For example, if the first set of partial incisions is half the size of the first set of incisions, then the second set of partial incisions may also be half the size of the second set of incisions, or the second set of partial incisions may be equal in size to the second set of incisions. If the method 100 requires a third set of incisions, then the third set of partial incisions may be equal to or less than the size of the determined third set of incisions.

In the second execution of step 135, the second set of partial arcuate incisions is performed on the cornea by the cutting laser subsystem 44. Any incision subsequent to the first set of partial incisions may either deepen the first set of partial incisions or be formed parallel to the first set of partial incisions and will produce a GUI display similar to that of FIG. 4B.

A third corneal topography measurement is performed by the measurement system at step 140 and is used at step 145 to determine if further incisions are necessary. The closed loop control of astigmatism treatment provided by method 100 adjusts for patient variability that are unaccounted for in nomograms, thereby providing improved surgical outcomes.

Another example astigmatism treatment is described below to illustrate the steps performed in method 100. After positioning the patient within the laser eye surgery system 2 in step 105 and measuring a corneal topography in step 110, the system 2 can determine that the radius of curvature of the cornea is 7.8 mm along the steep axis of 75 degrees. Step 120 determines by nomogram that the target curvature to correct the astigmatism is radius of curvature of 7.3 mm along the 75 degree axis. Then step 125 determines that the difference between the target curvature of 7.8 mm and measured curvature of 7.3 mm is 0.5 mm. In step 130, a first set of arcuate incisions are determined that is intended to achieve the 7.3 mm curvature. Then, in step 135, the first set of partial incisions corresponding to a 50% uncertainty level of the nomogram for the first set of arcuate incisions are determined. This first set of partial arcuate incisions is smaller than the first set of incisions determined in step 130, and is incised in the cornea. A second corneal topography measurement performed in step 140 determines that the radius of curvature is now 7.5 mm, which is 0.3 mm flatter than at the outset, but still 0.2 mm steeper than the target curvature. A second set of arcuate incisions is determined and carried out in steps 130 and 135 so as to deepen the first set of partial incisions. At step 140, a third corneal topography measurement is performed with the measured radius of curvature along 75 degrees matching the target curvature of 7.3 mm, thereby completing the astigmatism treatment.

In some embodiments, the system 2 can be configured to look for a volume of bubbles created as part of the treatment and/or nomogram and combined with keratometry measurements. The effect of bubbles can be determined experimentally, and a relationship of bubble size on outcome determined. For example, bubble size may be proportional to the effect on the outcome. In a second corneal topography measurement, a volume of bubbles formed may be measured responsive to the set of partial incisions formed in the cornea.

Although the above steps show method 100 providing laser eye treatment in accordance with many embodiments, a person of ordinary skill in the art will recognize many variations based on the teaching described herein. The steps may be completed in a different order, and one or more of the steps may comprise substeps. Steps may be added or deleted. Many of the steps may be repeated as often as beneficial to the method. The method 100 is not limited to correction of astigmatism, and may be modified for other treating higher order eye aberrations.

One or more of the steps of the method 100 may be performed with the circuitry as described herein, for example, one or more the processor or logic circuitry such as the programmable array logic for field programmable gate arrays. The circuitry may be programmed to provide one or more of the steps of method 100, and the program may comprise program instructions stored on a tangible computer readable memory or programmed steps of the logic circuitry such as the programmable array logic or the field programmable gate array, for example. In many embodiments, the processor comprises a plurality of processors and may comprise a plurality of distributed processors.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention. As used herein, the terms first and second are used to describe structures and methods without limitation as to the order of the structures and methods which can be in any order, as will be apparent to a person of ordinary skill in the art based on the teachings provided herein.

While certain illustrated embodiments of this disclosure have been shown and described in an exemplary form with a certain degree of particularity, those skilled in the art will understand that the embodiments are provided by way of example only, and that various variations can be made without departing from the spirit or scope of the invention. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

What is claimed is:

1. A method of treating an eye, comprising:
   measuring a first corneal topography of the eye;
   determining a first curvature of the cornea based on the first corneal topography, and determining a target curvature of the cornea that treats the eye;
   determining a first set of incisions in the cornea to achieve the target curvature of the cornea;

determining a first set of first partial incisions in the cornea, wherein the first partial incisions are smaller than the incisions of the first set of incisions;

performing the first set of first partial incisions on the cornea by a laser;

measuring a second corneal topography after performing the first set of first partial incisions;

determining a second curvature of the cornea based on the second corneal topography;

determining whether the second curvature differs from the target curvature by more than a threshold which indicates that the second curvature matches the target curvature;

when it is determined that the second curvature and the target curvature do not differ by more than the threshold, then ending treatment of the eye; and when it is determined that the second curvature and the target curvature differ by more than the threshold, then:
  determining a second set of incisions in the cornea different from the first set of incisions to achieve the target curvature in the cornea;
  determining a second set of second partial incisions in the cornea, wherein the second partial incisions of the second set of partial incisions are equal to or smaller than the incisions of the second set of incisions; and
  performing the second set of second partial incisions on the cornea by the laser.

2. The method of claim 1, further comprising:

measuring a third corneal topography after performing the second set of second partial incisions;

determining a third curvature of the cornea on the basis of the third corneal topography;

determining whether the third curvature differs from the target curvature by more than the threshold;

when it is determined that the third curvature and the target curvature do not differ by more than the threshold, then ending treatment of the eye; and when it is determined that the third curvature and the target curvature differ by more than the threshold, then:
  determining a third set of incisions to achieve the target curvature in the cornea;
  determining a third set of third partial incisions in the cornea, wherein the third partial incisions of the third set of partial incisions are equal to or smaller than the incisions of the third set of incisions; and
  performing the third set of third partial incisions on the cornea.

3. The method of claim 2, wherein the first partial incisions are one half a size of the incisions of the first set of incisions.

4. The method of claim 1, wherein the first partial incisions are one half a size of the incisions of the first set of incisions.

5. The method of claim 1, wherein the first set of incisions and the second set of incisions are based on a nomogram.

6. The method of claim 5, further comprising:
determining the first set of first partial incisions based on a predetermined uncertainty level of the nomogram.

7. The method of claim 1, wherein the second set of second partial incisions overlaps the first set of first partial incisions so as to deepen the first set of first partial incisions.

8. The method of claim 1, wherein the second set of partial incisions are parallel to the first set of partial incisions.

9. The method of claim 1, wherein the corneal topography measurement uses optical coherence tomography imaging.

10. The method of claim 1, wherein the second corneal topography measures a volume of bubbles formed as a result of the first set of first partial incisions.

11. The method of claim 1, wherein the laser is a femtosecond laser.

12. The method of claim 1, wherein the method treats higher order aberrations of the eye.

* * * * *